United States Patent [19]

Frisch et al.

[11] Patent Number: 5,376,621
[45] Date of Patent: Dec. 27, 1994

[54] AQUEOUS DISPERSIBLE CONCENTRATE CONTAINING LINURON AS ACTIVE INGREDIENT

[75] Inventors: Gerhard Frisch, Wehrheim; Thomas Maier, Frankfurt, both of Germany

[73] Assignee: Hoechst Aktiengesellschaft, Frankfurt am Main, Germany

[21] Appl. No.: 134,253

[22] Filed: Oct. 8, 1993

[30] Foreign Application Priority Data

Oct. 13, 1992 [DE] Germany .................. 4234464

[51] Int. Cl.⁵ ............................................. A01N 47/30
[52] U.S. Cl. .................................... 504/330; 504/116; 71/DIG. 1
[58] Field of Search ..................... 504/330, 116; 71/DIG. 1

[56] References Cited

U.S. PATENT DOCUMENTS

| | | | |
|---|---|---|---|
| 3,987,187 | 10/1976 | Albrecht et al. | 514/459 |
| 4,441,694 | 10/1983 | Smith, Jr. et al. | 71/DIG. 1 |
| 4,441,919 | 4/1984 | Albrecht et al. | 71/DIG. 1 |
| 5,226,945 | 7/1993 | Frisch | 504/148 |

FOREIGN PATENT DOCUMENTS

| | | |
|---|---|---|
| 4100589 | 3/1990 | Australia . |
| 2018580 | 12/1990 | Canada . |
| 0281398 | 7/1988 | European Pat. Off. . |
| 0402769 | 12/1990 | European Pat. Off. . |
| 0481404 | 4/1992 | European Pat. Off. . |
| 0505053 | 9/1992 | European Pat. Off. . |
| 2323435 | 4/1977 | France . |
| 2447748 | 8/1980 | France . |
| 2301922 | 8/1974 | Germany . |
| 0017879 | 10/1980 | Germany . |
| 0357559 | 3/1990 | Germany . |
| 1551829 | 9/1979 | United Kingdom . |

Primary Examiner—Richard L. Raymond
Assistant Examiner—Brian G. Bembenick
Attorney, Agent, or Firm—Curtis, Morris & Safford

[57] ABSTRACT

Herbicides comprising from 1 to 50% by weight of linuron, from 0.1 to 25% by weight of a mixture composed of substituted phenols and polyvinylpyrrolidone in a ratio of from 1:100 to 100:1, from 0.5 to 20% by weight of a ligninsulfonate, from 0.1 to 10% by weight of a salt of a polymerized alkylnaphthalenesulfonic acid, and from 20 to 80% by weight of water.

8 Claims, No Drawings

AQUEOUS DISPERSIBLE CONCENTRATE CONTAINING LINURON AS ACTIVE INGREDIENT

The present invention relates to an aqueous herbicidal dispersible concentrate which contains linuron as active ingredient.

The herbicide 3-(3,4-dichlorophenyl)-1-methoxy-1-methylurea is already known, as mixed formulations in the form of wettable powders and as formulations in the form of emulsifiable concentrates (commercial product ®Afalon S from HOECHST AG) and suspension concentrates, the latter having the advantage that they neither form dusts nor are inflammable. However, formulations involving the aqueous dispersion variant have given problems with regard to the crystalline growth of linuron.

Mixed formulations are also known in which linuron, in combination with other herbicides, exhibits almost no crystalline growth (EP-A-0 402 769; EP-A-0 481 404).

Formulations are also known, some of which contain linuron, in which dyes are used to inhibit the growth of crystals (EP-A-17 879, U.S. Pat. No. 4,441,919, DE-A-2,301,922, U.S. Pat. No. 3,987,187 and DE-A-4,013,524).

The known aqueous dispersible concentrates which contain dye have considerable disadvantages (U.S. Pat. No. 4,441,919). After the preparation of the above-mentioned dispersible concentrates, the production plant, application equipment and containers must in a laborious operation be rinsed, often a number of times, to remove residues of the fat-soluble dyes which adhere to them. In production plant, application equipment and containers which are used for more than one function, the abovementioned disadvantages are a particular problem and give rise, after laborious cleaning, to cleaning fluids which are contaminated with fat-soluble dyes and which have to be disposed of.

It is known, moreover, that certain substituted phenols prevent, or severely reduce, the growth of crystals or the crystallization of active substances in organic-/aqueous emulsions, although in this case it is necessary for the active ingredient to be present in the oil phase (EP-A-0 357 559).

The object of the invention was therefore to prepare aqueous dispersions of linuron, which has a solubility in water of 81 mg/kg at 24° C., which dispersions, although free from dyes inhibiting crystalline growth, should also exhibit no crystalline growth on storage in the temperature range from −10° C. to 50° C. over more than 3 months.

It has now been found that, surprisingly, a mixture of substituted phenols and polyvinylpyrrolidone, in particular ®Luviskol K grades, in a ratio of from 1:100 to 100:1, but preferably from 1:20 to 20:1 and in particular from 1:20 to 10:1, the total proportion of this mixture ranging from 0.1 to 25% but being preferably from 0.5 to 12%, achieves this desired effect and does so preferentially for specific dispersible concentrates of linuron. Even for monolinuron, which is a closely related molecule in chemical terms, the inhibitory effect on crystalline growth is decidedly low.

The phenols used in the aqueous dispersible concentrates according to the invention are mono-, di- or tri-substituted ($C_1$–$C_{10}$)-alkylphenols, preferably trisubstituted ($C_1$–$C_{10}$)-alkylphenols and in particular tributylphenol. The polyvinylpyrrolidones also include, inter alia, polyvinylpyrrolidones which are substituted in the ortho or para position and which have different viscosities in water.

The present invention therefore relates to an aqueous dispersible concentrate comprising
  a) from 1 to 50% by weight, preferably 8 to 45% by weight of linuron,
  b) from 0.1 to 25% by weight, preferably from 0.5 to 12% by weight of substituted phenols and polyvinylpyrrolidones mixed in a ratio of from 1:100 to 100:1, preferably from 1:20 to 20:1 and in particular from 1:20 to 10:1,
  c) from 0.5 to 20% by weight, preferably from 0.5 to 6% by weight and in particular from 0.5 to 4% by weight of a ligninsulfonate,
  d) from 0.1 to 10% by weight, preferably from 0.1 to 5% by weight and in particular from 0.1 to 3% by weight of a salt of a polymerized alkylnaphthalenesulfonic acid, and
  e) from 20 to 80% by weight, preferably from 30 to 65% by weight of water.

Linuron (component a) as the active ingredient is present predominantly as a dispersed solid and to only a small extent in dissolved form.

The compounds contained in the herbicidal formulations according to the invention are composed principally of the above-mentioned components a) to e) wherein the substituted phenol/polyvinylpyrrolidone mixture (b) is essential in accordance with the invention to prevent the crystalline growth of linuron (a)in a ready-to-use mixture which also contains components (c), (d)and (e).

In addition to these five components, said ready-to-use mixture can also contain up to 25% by weight, preferably between 0.1 and 25% by weight and in particular from 0.1 to 15% by weight of conventional auxiliaries.

Examples of such auxiliaries are wetting agents, such as sodium salts of ($C_{12}$–$C_{14}$)-alkyl ether sulfates containing to 3 EO (EO=ethyleneoxy units) (e.g. ®Genapol LRO, Hoechst AG), antifoams, preferably based on silicone (for example the antifoam series from Rhône-Poulenc or antifoam SH from Wacker), inorganic and-/or organic thickeners, based for example on aluminosilicate, xanthan, methylcellulose (e.g. the commercial products ®Tylose from HOECHST AG), polysaccharide (e.g. the commercial products ®Rhodopol 23 from Rhône-Poulenc), alkaline earth metal silicate, gelatine and polyvinyl alcohol (e.g. the commercial products ®Mowiol from HOECHST AG), preservatives, for example those based on formaldehyde, benzoic acid and triphenyltin or isothiazolinone (e.g. the commercial product ®Mergal WP1 from Riedel de Hëan), antifreeze agents and additives preventing loss by drying, for example urea and polyols such as glycol, propylene glycol, glycerol and sugar.

Combinations which, in the case according to the invention, effectively suppress crystalline growth of linuron, are preferably those which contain as component (b) a mixture of tributylphenol and polyvinylpyrrolidone (e.g. ®Luviskol K30), (c) ligninsulfonates in their possible salt forms, e.g. ®Vanisperse CB and/or ®Ufoxane 3A from Borregaard, Sarpsborg, Norway, and as component (d) an Na salt of a polymerized alkylnaphthalenesulfonic acid such as ®Darvan No. 3 (R. T. Vanderbilt Comp. Norwalk, CT 06855, USA data sheet 07.01.81).

For the preparation of the dispersible concentrates according to the invention, the components are stirred with water, the coarse suspension obtained is comminuted, if appropriate by grinding in a corundum or toothed-disk mill to particle sizes of approximately 200 micron, and the product is subsequently milled in attrition ball mills or sand mills until the particles of the dispersion are present in sizes of from 0.1 to 10 micron and preferably less than 5 micron. The particle sizes can be determined using a disk centrifuge or by laser diffraction.

The use of the dispersible concentrates according to the invention for controlling unwanted plant growth takes place in a simple manner by diluting the dispersible concentrates, if appropriate with the desired amount of water, to give a spray liquor which is briefly stirred, and applying an effective quantity of the formulation according to the invention to the unwanted plants or to the areas or substrates which are affected by them, or to the seed.

The examples which follow are intended to illustrate the invention.

Carrying out experiments (see Examples 1 to 5, Table 1), in which either the substituted phenol derivative is replaced by another product in the presence of polyvinylpyrrolidone, or in which the polyvinylpyrrolidone derivative is replaced by another conventional auxiliary while retaining the substituted phenol derivative, a high degree of crystalline growth is evident even after storing the corresponding dispersion for only a very short time, leading to undesirable sedimentation of the linuron crystals.

Table 1 below lists examples of the effects described here, without limiting the scope of the invention.

Comparison Examples 1 to 3

In the Comparison Examples 1 to 3 (Table 1), aqueous herbicidal dispersible concentrates were prepared as described and stored at temperatures of between $-10°$ C. and $50°$ C. for a period of 3 months, after which the crystalline growth and the storage-stability of the dispersible concentrate was investigated and assessed.

Comparison Examples 4 and 5

Aqueous herbicidal dispersible concentrates were prepared as before but using in each case only one of the additives (b) according to the invention. After storage as described above, the crystalline growth and the storage-stability were investigated, with storage-stability being poor and crystalline growth being moderate to high.

Examples 6 to 14

The aqueous herbicidal dispersible concentrate prepared in accordance to the invention, which contains both constituents of component (b) according to the invention, exhibits excellent storage-stability and no crystalline growth after being stored for 3 months at temperatures from $-10°$ C. to $50°$ C.

TABLE 1

| Example No. | 1 | 2 | 3 | 4 | 5 | 6 | 7 | 8 | 9 |
|---|---|---|---|---|---|---|---|---|---|
| Linuron 96% | 40.0% | 40.0% | 40.0% | 43.8% | 43.8% | 43.8% | 43.8% | 43.8% | 43.8% |
| Glycerol | 10.0% | 10.0% | 10.0% | 10.0% | 10.0% | 10.0% | 10.0% | 10.0% | 10.0% |
| Silcolapse 5020 (1) | 1.0% | 1.0% | 1.0% | 1.0% | 1.0% | 2.0% | 2.0% | 2.0% | 2.0% |
| Mergal WP 1 (2) | 0.1% | 0.1% | 0.1% | 0.1% | 0.1% | 0.1% | 0.1% | 0.1% | 0.1% |
| Rhodopol 23 (3) | 0.15% | 0.15% | 0.15% | 0.1% | 0.1% | 0.1% | 0.1% | 0.15% | 0.1% |
| Darvan No. 3 (4) | 1.0% | 1.0% | 1.0% | 1.0% | 1.0% | 1.0% | 1.0% | 1.0% | 1.0% |
| Vanisperse CB (5) | 4.0% | 1.0% | 2.0% | 1.0% | 3.0% | 3.0% | 3.0% | 3.0% | 3.0% |
| Tributylphenol | | | | | 0.5% | 0.5% | 1.0% | 0.5% | 0.5% |
| Luviskol K 30 (6) | | | | 0.5% | | 0.5% | 1.0% | 0.5% | 0.5% |
| HOE S 1728 | | 8.0% | | | | | | | |
| Galoryl DT 201 (7) | | | 2.0% | | 0.5% | | | | |
| Ufoxane 3 A (8) | | | | | | | | | 1.0% |
| Water up to | 100% | 100% | 100% | 100% | 100% | 100% | 100% | 100% | 100% |
| Storage test | unstable | unstable | unstable | unstable | unstable | stable | stable | stable | stable |
| Crystalline growth | high | high | mod. | mod. | high | none | none | none | none |

| Example No. | 10 | 11 | 12 | 13 | 14 |
|---|---|---|---|---|---|
| Linuron 96% | 43.8% | 43.8% | 43.8% | 43.8% | 43.8% |
| Glycerol | 10.0% | 10.0% | 10.0% | 10.0% | 10.0% |
| Silcolapse 5020 (1) | 2.0% | 2.0% | 2.0% | 2.0% | 2.0% |
| Mergal WP 1 (2) | 0.1% | 0.1% | 0.1% | 0.1% | 0.1% |
| Rhodopol 23 (3) | 0.1% | 0.1% | 0.1% | 0.1% | 0.1% |
| Darvan No. 3 (4) | 1.0% | 1.0% | 1.0% | 1.0% | 1.0% |
| Vanisperse CB (5) | 3.0% | 3.0% | 3.0% | 3.0% | 3.0% |
| Tributylphenol | 0.5% | 0.5% | 0.1% | 1.0% | 5.0% |
| Luviskol K 30 (6) | 2.5% | 5.0% | 5.0% | 2.5% | 0.5% |
| HOE S 1728 | | | | | |
| Galoryl DT 201 (7) | | | | | |
| Uufoxane 3 A (8) | 1.0% | 1.0% | 1.0% | 1.0% | 1.0% |
| Water up to | 100% | 100% | 100% | 100% | 100% |
| Storage test | stable | stable | stable | stable | stable |

TABLE 1-continued

| Crystalline growth | none | none | none | none | none |
| --- | --- | --- | --- | --- | --- |

Notes on Table 1
(1) Antifoam based on silicone, commercial product ®Silcolapse 5020 from Rhône-Poulenc;
(2) Preservative, commercial product from Riedel de Haën
(3) Commercial product ®Rhodopol 23 from Rhône-Poulenc, a thickener based on polysaccharide;
(4) Commercial product ®Darvan No. 3 from R.T. Vanderbilt Comp. Norwalk, CT 06855, USA data sheet 07.01.81, based on an Na salt of polymerized substituted alkylbenzenesulfonic acids;
(5) Commercial product ®Vanisperse CB from Borregaard Industries Ltd., Sarpsborg, Norway; a ligninsulfonate containing 0.17 sulfonic acid groups per phenylpropane unit, a total sulfur content of 2.4% and a pH of 8.8 (as 3% strength solution);
(6) ®Luviskol K30, commercial product from BASF, Ludwigshafen;
(7) Commercial product ®Galoryl DT201 from CFPI (condensed sulfonic acids in the form of the sodium salts);
(8) Commercial product ®Ufoxane from Borregaard Industries Ltd., Sarpsborg, Norway; based on sodium ligninsulfonate (degree of sulfonation 0.4).

It can be seen from Table 1 that the combination of substituted phenol and polyvinylpyrrolidone enable the successful preparation of storage-stable dispersions of linuron with a high content of the active ingredient, which, after storage for more than 3 months in the temperature range from $-10°$ C. to $50°$ C., were stable and showed no crystalline growth.

We claim:

1. A herbicidal formulation comprising
   a) from 1 to 50% by weight of linuron,
   b) from 0.1 to 25% by weight of a mixture composed of substituted phenols and polyvinylpyrrolidone in a ratio of from 1:100 to 100:1,
   c) from 0.5 to 20% by weight of a ligninsulfonate,
   d) from 0.1 to 10% by weight of a salt of a polymerized alkylnaphthalenesulfonic acid, and
   e) from 20 to 80% by weight of water.
2. A formulation as claimed in claim 1, which comprises
   a) from 8 to 45% by weight of linuron,
   b) from 0.5 to 12% by weight of a mixture composed of substituted phenols and polyvinylpyrrolidone in a ratio of from 1:20 to 20:1,
   c) from 0.5 to 6% by weight of a ligninsulfonate,
   d) from 0.1 to 5% by weight of a salt of a polymerized alkylnaphthalenesulfonic acid, and
   e) from 30 to 65% by weight of water.
3. A formulation as claimed in claim 1, which comprises
   a) from 8 to 45% by weight of linuron,
   b) from 0.5 to 5.5% by weight of a mixture composed of substituted phenols and polyvinylpyrrolidone in a ratio of from 1:20 to 10:1,
   c) from 0.5 to 4% by weight of a ligninsulfonate,
   d) from 0.1 to 3% by weight of a salt of a polymerized alkylnaphthalenesulfonic acid, and
   e) from 30 to 65% by weight of water.
4. A formulation as claimed in claim 1, which comprises from 0.1 to 25% by weight of conventional auxiliaries from the group consisting of wetting agents, antifoams, thickeners, preservatives, antifreeze agents and additives preventing loss by drying.
5. A formulation as claimed in claim 1, which comprises as the substituted phenol a mono-, di- or trisubstituted $(C_1-C_{18})$-alkylphenol.
6. A formulation as claimed in claim 5, which comprises as the substituted phenol a trisubstituted $(C_1-C_{10})$-alkylphenol.
7. A formulation as claimed in claim 6, which comprises as the substituted phenol tributylphenol.
8. A method of controlling unwanted plant growth, which comprises applying to the plants or to the areas or substrates affected by them or to the seed an effective amount of a formulation, diluted with water if desired, as defined in claim 1.

* * * * *